US010005936B2

(12) United States Patent
Steele et al.

(10) Patent No.: US 10,005,936 B2
(45) Date of Patent: Jun. 26, 2018

(54) PHOTOACTIVE BIOADHESIVE COMPOSITIONS

(71) Applicant: Nanyang Technological University, Nanyang (SG)

(72) Inventors: W. J. Terry Steele, Nanyang (SG); Vladislav Papper, Nanyang (SG); Robert S. Marks, Nanyang (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 0 days. days.

(21) Appl. No.: 14/646,445

(22) PCT Filed: Nov. 21, 2013

(86) PCT No.: PCT/SG2013/000492
§ 371 (c)(1),
(2) Date: May 21, 2015

(87) PCT Pub. No.: WO2014/081391
PCT Pub. Date: May 30, 2014

(65) Prior Publication Data
US 2015/0315434 A1    Nov. 5, 2015

Related U.S. Application Data

(60) Provisional application No. 61/729,504, filed on Nov. 23, 2012.

(51) Int. Cl.
| C09J 167/04 | (2006.01) |
| C09J 105/04 | (2006.01) |
| A61N 5/06 | (2006.01) |
| C09J 189/00 | (2006.01) |
| C08K 9/04 | (2006.01) |
| C08K 9/02 | (2006.01) |
| A61K 31/715 | (2006.01) |
| A61K 31/734 | (2006.01) |
| C08G 63/685 | (2006.01) |
| A61L 24/00 | (2006.01) |
| A61L 24/04 | (2006.01) |

(Continued)

(52) U.S. Cl.
CPC ........... *C09J 167/04* (2013.01); *A61K 9/0014* (2013.01); *A61K 9/0024* (2013.01); *A61K 31/715* (2013.01); *A61K 31/734* (2013.01); *A61K 33/00* (2013.01); *A61K 45/06* (2013.01); *A61L 24/001* (2013.01); *A61L 24/0031* (2013.01); *A61L 24/046* (2013.01); *A61N 5/062* (2013.01); *C08B 11/08* (2013.01); *C08B 15/00* (2013.01); *C08B 31/00* (2013.01); *C08B 33/00* (2013.01); *C08B 35/00* (2013.01); *C08B 37/00* (2013.01); *C08B 37/003* (2013.01); *C08B 37/0021* (2013.01); *C08B 37/0057* (2013.01); *C08B 37/0072* (2013.01); *C08B 37/0075* (2013.01); *C08B 37/0084* (2013.01); *C08G 63/6852* (2013.01); *C08H 1/06* (2013.01); *C08J 5/128* (2013.01); *C08K 9/02* (2013.01); *C08K 9/04* (2013.01); *C09J 101/08* (2013.01); *C09J 101/284* (2013.01); *C09J 103/04* (2013.01); *C09J 103/14* (2013.01); *C09J 105/00* (2013.01); *C09J 105/02* (2013.01); *C09J 105/04* (2013.01); *C09J 105/08* (2013.01); *C09J 105/10* (2013.01); *C09J 189/00* (2013.01); *C09J 189/06* (2013.01); *C09J 201/025* (2013.01); *A61L 2430/34* (2013.01); *C08J 2300/16* (2013.01); *C08J 2367/04* (2013.01); *C08J 2389/00* (2013.01); *C08J 2400/106* (2013.01); *C08L 2205/16* (2013.01)

(58) Field of Classification Search
CPC ......... C09J 167/04; C09L 105/04; A61N 5/06
See application file for complete search history.

(56) References Cited

U.S. PATENT DOCUMENTS 5,679,559 A * 10/1997 Kim ................. A61K 47/48315
428/402.2
6,713,524 B2 * 3/2004 Leukel .................... A61L 27/34
522/1

(Continued)

FOREIGN PATENT DOCUMENTS

| EP | 0 330 344 A2 | 8/1989 |
| WO | 02/13881 A1 | 2/2002 |
| WO | 2004/067044 A2 | 8/2004 |
| WO | 2005/052580 A1 | 6/2005 |
| WO | 2008/023170 A1 | 2/2008 |
| WO | 2009/097152 A1 | 8/2009 |
| WO | 2010/100410 A1 | 9/2010 |
| WO | 2010/100413 A2 | 9/2010 |

OTHER PUBLICATIONS

Lösel et al. (European Cells and Materials vol. 20(3); (2010)162).*

(Continued)

Primary Examiner — Shirley V Gembeh
(74) Attorney, Agent, or Firm — Riverside Law LLP

(57) ABSTRACT

A novel diazirine-based biocompatible polymer that can be used as on-demand or tunable bioadhesive and applied across various clinically important surfaces. The biocompatible polymer comprises a single strand of repeating units and up to 5,000 photoreactive diazirine groups covalently attached to it. A bioadhesive composition comprises the polymer of the present invention and suitable solvents, surfactants, stabilizers, fillers and other additives. The composition may additionally contain metallic particles of size less than 50 micron made of rare earth elements and has UV or NIR transparency less than 1 optical density unit per 1 centimeter. The poly-diazirine surface grafted thin films can be used for minimally invasive surgeries.

30 Claims, 6 Drawing Sheets

(51) Int. Cl.

| | | |
|---|---|---|
| C09J 105/10 | (2006.01) | |
| C08B 11/08 | (2006.01) | |
| C08B 15/00 | (2006.01) | |
| C08B 31/00 | (2006.01) | |
| C08B 33/00 | (2006.01) | |
| C08B 35/00 | (2006.01) | |
| C08B 37/00 | (2006.01) | |
| C08B 37/02 | (2006.01) | |
| C08B 37/08 | (2006.01) | |
| C08H 1/06 | (2006.01) | |
| C09J 101/08 | (2006.01) | |
| C09J 101/28 | (2006.01) | |
| C09J 103/04 | (2006.01) | |
| C09J 103/14 | (2006.01) | |
| C09J 105/00 | (2006.01) | |
| C09J 105/02 | (2006.01) | |
| C09J 105/08 | (2006.01) | |
| C09J 189/06 | (2006.01) | |
| A61K 45/06 | (2006.01) | |
| A61K 33/00 | (2006.01) | |
| A61K 9/00 | (2006.01) | |
| C09J 201/02 | (2006.01) | |
| C08J 5/12 | (2006.01) | |

(56) References Cited

U.S. PATENT DOCUMENTS

2002/0022013 A1* 2/2002 Leukel .................. A61L 27/14
424/78.17

2003/0113279 A1* 6/2003 Vic .......................... A61K 8/35
424/59
2007/0053642 A1* 3/2007 Mishra ............... G02B 6/02014
385/127

OTHER PUBLICATIONS

In view of Döring et al. (The EMBO Journal; 13(11)2677-2685; (1994).*

Bond et al., "Photocrosslinking of glycoconjugages using metabolically incorporated diazirine-containing sugars," *Nature Protocols*, 2009, 4(7)1044-1063.

Freichels et al., "Synthesis of Poly(lactide-co-glycolide-co-ε-caprolactone)-graft-mannosylated Poly(ethylene oxide) Copolymers by Combination of "Clip" and "Click" Chemistries," *Biomacromolecules*, 2012, 13:760-768.

Haeussinger et al., "Simulation of Near-Infrared Light Absorption Considering Individual Head and Prefrontal Cortex Anatomy: Implications for Optical Neuroimaging," *PLoS One*, Oct. 2011, 6(10):e26377.

Hashizume et al., "Morphological and mechanical characteristics of the reconstructed rat abdominal wall following use of a wet electrospun biodegradable polyurethane elastomer scaffold," *Biomaterials*, 2010, 31:3253-3265.

Prendergast et al., "Analysis of Prolapse in Cardiovascular Stents: A Constitutive Equation for Vascular Tissue and Finite-Element Modelling," *ASME*, Oct. 2003, 125:692-699.

Vetrone et al., "Near-Infrared-to-Blue Upconversion in Colloidal $BaYF_5:Tm^{3+}$, $Yb^{3+}$Nanocrystals," *Chem. Mater.*, 2009, 21:1847-1851.

International Search Report for PCT/SG2013/000492 dated Mar. 19, 2014.

* cited by examiner

PHOTOACTIVE BIOADHESIVE COMPOSITIONS

CROSS-REFERENCE TO RELATED APPLICATIONS

This application is the U.S. national phase application filed under 35 U.S.C. § 371 claiming benefit to International Patent Application No. PCT/SG2013/000492, filed on Nov. 21, 2013, which is entitled to priority under 35 U.S.C. § 119(e) to U.S. provisional application Ser. No. 61/729,504, filed Nov. 23, 2012, the disclosures of which are incorporated herein by reference in their entirety.

FIELD OF THE INVENTION

The present invention relates to photoactive bioadhesive compositions containing diazirine derivatives in general, and to their use in tissue fixation, in particular.

BACKGROUND OF THE INVENTION

Current methods of tissue fixation leave much to be desired; essentially relying on technologies developed from the clothing and carpentry industries. Screws, pins, wires, sutures, and buttress plates, are examples of bone and soft tissue fixation implants. These devices have many disadvantages, including the need for subsequent operations for removal and interference with mobility and growth impediments in youths. They also have high rates of complications, such as infection and tissue inflammation.

With the market value of fixation devices estimated at approximately four billion dollars, many attempts have been made to improve upon these implants. Resorbable implants have made inroads in addressing some of the issues above, however they still have problems with the destructive nature of the mechanical fixation. For example, the trauma induced by resorbable suturing on intestinal tissue upregulates enzymes that breakdown collagen (the structural component) for up to 4 days post-procedure—weakening the intestine tissue and raising the probabilities of tears and intestinal leakages—but it's still the standard operating procedure for intestinal anastomoses. Intestinal anastomoses are typically performed for treatment of colorectal cancer.

'Gluing' soft-tissues and biomaterials together is far more convenient than sutures and conventional tissue fixation, but development of a suitable bioadhesive has yet to be fully realized. Bioadhesive 'glues' are a significant engineering hurdle in numerous fields including wound closures, implantable electronics, meshes for abdominal surgeries, and tissue engineering transplants. Medical grade cyanoacrylates, for example Dermabond® and Super Glue®, and fibrin tissue adhesives, for example Tisseal® and Evicel®, are currently the only commercially available and FDA approved bioadhesives that have addressed soft tissue fixation. Unfortunately, they trade adhesive strength for biocompatibility or vice versa. Cyanoacrylates typically have strong tissue adhesion, but are relatively inflexible. Their brittleness, combined with local tissue toxicity and incapability of local drug delivery limits them to skin and other topical adhesions. Fibrin-based tissue adhesives have many shortcomings as well. Their bioadhesion is 'hydrogel' weak, has potential neurotoxicity complications and serious religious concerns due to the predominantly human (or bovine) fibrinogen and thrombin sources. Due to their weak mechanical properties, fibrin tissues adhesives are best suited for control of bleeding.

WO/2010/100410 and WO/2010/100413 disclose functionalized diazo derivatives, including diazopyruvate, and their use for producing a chemically-bound three-dimensional network on or within a substrate, but does not mention any particular application of said diazo compounds for tissue bioadhesion.

WO 2009/097152 relates to calcium-reactive amines and acrylic or methacrylic ester monomers adhesives, and use thereof for adhering dental and medical biomaterials to hard tissues via a molecular bridge formed from to hard tissues such as enamel, dentin, and bone. However, this publication does not mention, nor hint to use of photoactive compounds in bioadhesion, but merely mentions that the claimed formulation can contain light-activated free-radical initiators.

WO 2008/023170 describes a group of diazo compounds used as aryl carbene precursors for use in the process of producing a substrate having an adhesive surface, which allows the substrate to adhere to other materials to be tailored. Said publication however is silent about the use of diazirine derivatives in bioadhesive formulations for tissue fixation.

WO 2004/067044 provides a light-activated adhesive composite suitable for medical and surgical applications. The composite includes a scaffold based on various poly (alpha ester)s such as poly(lactic acid), poly(glycolic acid), poly(L-lactic-co-glycolic acid), poly(epsilon-caprolactone), poly(ethylene glycol), poly(ortho ester)s and poly(anhydrides), and a light-activated adhesive, such as a laser tissue solder incorporating chromophores, for example indocyanine green and methylene blue.

EP 0330344 relates to use of crosslinked collagen as a bioadhesive for sutureless closures of the skin and eye or as a superhydrated material for contact lenses, moist bandage contact lens, lens or corneal implant material, or as a drug delivery agent. According to EP 0330344, collagen, which is an example of amino-acid containing polymers, is crosslinked into a highly molecularly crosslinked product upon photoactivation with photoactive crosslinking reagents, such as diazo or azide derivatives.

Failure of soft tissue bioadhesives to address local tissue fixation and biocompatibility has prompted urgent need for a new bioadhesive that allows biomaterials to be adhered onto soft tissues while maintaining a high level of biocompatibility and adhesive strength.

SUMMARY OF THE INVENTION

Various embodiments of the invention provide photoactive bioadhesive compositions containing diazirine derivatives, and their use in tissue fixation.

In one embodiment, a biocompatible polymer comprises a single strand of repeating units and up to 5,000 photoreactive groups covalently attached to said strand, wherein said polymer has a molecular weight of up to 3 million Daltons, and wherein said photoreactive groups are derivatives of diazirine.

In a particular embodiment, said polymer can be any FDA-approved bioresorbable polymer selected from the group consisting of polyethylene glycol (PEG), PEG fatty acid esters, poly-L-lactic acid (PLLA), poly(lactide-co-glycolide) (PLGA), poly caprolactone (PCL), polyvinyl pyrrolidone (PVP), polyvinyl alcohol (PVA), collagen, chitosan, hydroxy propyl cellulose, polyamides, polyglycerol esters of fatty acids, polysaccharides, polyesters, and combinations thereof. The polysaccharide is selected from the group consisting of dextran, chitosan, heparin, hyaluronic acid, alginates, starch, glycogen, amylose, amylopectin, cellulose, xylan, and numerous other natural and synthetic polysaccharides.

In a further embodiment, the diazirine derivative is a compound of the following formula.

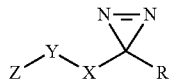

wherein
R is
a hydrogen;

$C_1$-$C_8$ straight-chain or branched alkyl group, $C_2$-$C_8$ straight-chain or branched alkenyl or alkynyl group, or phenyl group substituted at any ring position with one or more the same or different $C_1$-$C_8$ straight-chain or branched alkyl group, phenyl or heterocyclic ring, which may be optionally substituted with one or more the same or different $C_1$-$C_8$ straight-chain or branched alkyl group, $C_1$-$C_8$ alkoxy group, $C_1$-$C_8$ alkoxycarbonyl group, carboxyl group, hydroxyl group, nitro group, halogen atom or amino group optionally mono or di-substituted with the same or different C1-C8 straight-chain or branched alkyl group;

methyl group substituted with 1-3 halogen atoms;

amino group optionally mono or di-substituted with the same or different $C_1$-$C_8$ straight-chain or branched alkyl group;

thiol or thioether group having the same or different $C_1$-$C_8$ straight-chain or branched alkyl group;

sulfone or sulfate group having the same or different $C_1$-$C_8$ straight-chain or branched alkyl group;

nitro, cyano, halogen, hydroxy, carboxylic acid or sulfonic acid group; or alkoxy or alkoxycarbonyl group having the same or different $C_1$-$C_8$ straight-chain or branched alkyl group;

X is a bond or 5-7 membered saturated cyclic or heterocyclic, aromatic or heteroaromatic ring unsubstituted or mono-, di- or tri-substituted with:

$C_1$-$C_8$ straight-chain or branched alkyl group, $C_2$-$C_8$ straight-chain or branched alkenyl or alkynyl group, or phenyl group substituted at any ring position with one or more the same or different $C_1$-$C_8$ straight-chain or branched alkyl group, phenyl or heterocyclic ring, which may be optionally substituted with one or more the same or different $C_1$-$C_8$ straight-chain or branched alkyl group, $C_1$-$C_8$ alkoxy group, $C_1$-$C_8$ alkoxycarbonyl group, carboxyl group, hydroxyl group, nitro group, halogen atom or amino group optionally mono or di-substituted with the same or different $C_1$-$C_8$ straight-chain or branched alkyl group;

methyl group substituted with 1-3 halogen atoms;

amino group optionally mono or di-substituted with the same or different $C_1$-$C_8$ straight-chain or branched alkyl group;

thiol or thioether group having the same or different $C_1$-$C_8$ straight-chain or branched alkyl group;

sulfone or sulfate group having the same or different $C_1$-$C_8$ straight-chain or branched alkyl group;

nitro, cyano, halogen, hydroxy, carboxylic acid or sulfonic acid group; or alkoxy or alkoxycarbonyl group having the same or different $C_1$-$C_8$ straight-chain or branched alkyl group;

Y is a bond or saturated and unsaturated $C_1$-$C_{500}$ straight-chain or branched alkyl, alkenyl or alkynyl group, wherein said chain may optionally incorporate at least one hetero atom, and may also comprise at least one substituent;

Z is any suitable functional group, such as halogen, amino, cyano, hydroxy, aldehyde, alkoxycarbonyl, N-amide, N-hydroxysuccinimide ester, maleimide or thiol.

In a specific embodiment, diazirine derivative can be selected from the list of:
3-phenyl-3-trifluoromethyl-3H-diazirine,
3-[3-(bromoacetylamino)phenyl]-3-trifluoromethyl-3H-diazirine,
3-[4-(bromoacetylamino)phenyl]-3-trifluoromethyl-3H-diazirine,
3-[2-methoxy,5-(bromoacetylamino)phenyl]-3-trifluoromethyl-3H-diazirine,
3-[2-cyano,5-(bromoacetylamino)phenyl]-3-trifluoromethyl-3H-diazirine,
3-[2-sulfo,5-(bromoacetylamino)phenyl]-3-trifluoromethyl-3H-diazirine,
3-[3-(bromomethyl)phenyl]-3-trifluoromethyl-3H-diazirine,
3-[4-(bromomethyl)phenyl]-3-trifluoromethyl-3H-diazirine,
3-[2-methoxy,5-(bromomethyl)phenyl]-3-trifluoromethyl-3H-diazirine,
3-[2-cyano,5-(bromomethyl)phenyl]-3-trifluoromethyl-3H-diazirine,
3-[2-sulfo,5-(bromomethyl)phenyl]-3-trifluoromethyl-3H-diazirine,
3-[3-aminophenyl]-3-trifluoromethyl-3H-diazirine,
3-[4-aminophenyl]-3-trifluoromethyl-3H-diazirine,
3-[2-methoxy,5-aminophenyl]-3-trifluoromethyl-3H-diazirine,
3-[2-cyano,5-aminophenyl]-3-trifluoromethyl-3H-diazirine, and
3-[2-sulfo,5-aminophenyl]-3-trifluoromethyl-3H-diazirine.

In another embodiment, a bioadhesive composition comprises the polymer of the present invention and suitable solvents, surfactants, stabilizers, fillers and other additives. The additives may be anti-inflammatory drugs, anti-proteases, antibiotics, and/or anti-restenosis compounds.

In yet further embodiment, the composition can be in a form of hydrogel, biocompatible film, patch or bondage. In addition, the composition may contain metallic particles of size less than 50 micron made of rare earth elements, such as lanthanide group elements, including but not limited to scandium, yttrium, lanthanum, cerium, praseodymium, neodymium, promethium, samarium, europium, gadolinium, terbium, dysprosium, holmium, erbium, thulium, ytterbium, and lutetium. The composition is UV or NIR transparent, having transparency less than 1 optical density unit per 1 centimeter.

In additional embodiment, the metal particles can be coated with anionic or cationic coating comprising fatty acids, silica, polyethylene glycol, pluronics, poloxamers, polydopamine, polylysine or any suitable peptide.

In still additional embodiment, the composition may further comprise aligned nanofibers of biodegradable polymer, such as collagen or gelatin, for matching biomechanics of soft tissues. The soft tissues, such as of vein and arteries, are known to exhibit a non-linear anisotropy—the elastic modulus increases exponentially with strain in the radial-orientation, but not in the axial-orientation. Incorporation of the aligned nanofibers of biodegradable polymers within the matrix of the bioresorbable polymer, such as PLGA, can mimic this anisotropy of the tissue under treatment.

In another embodiment, the composition may further comprise any alginate-based polymer, such as alginate-pyrrole or alginate-biotin, thus providing additional properties to the biomaterial, such as increased affinity and conductivity.

In a general embodiment, the composition may be used in surgery, such as gastrointestinal surgery towards cancer removal, anastomoses (including end-to-end anastomoses) procedures, such as blood vessel anastomoses wherein two tubes or lumens must be joined, tissue fixation, suture sealing and replacement, treatment of lung punctures, body lumen punctures or leaks, cerebrospinal fluid membrane damages, obesity treatments, bowel obstructions, fixing flat electrodes to heart tissue during open heart surgery, and patches containing drugs such as in gastrointestinal system.

In still another embodiment, a method for the preparation of the polymer of the present invention comprises the steps of:
(a) Preparing a solution of said biocompatible polymer having concentration of 0.1 to 100 mg/ml at pH 7.2;
(b) Dissolving said diazirine compound in a suitable organic within the concentration range of 0.01 to 100 mM;
(c) Mixing and reacting the solution of said biocompatible polymer prepared in a) with the solution of the diazirine derivative prepared in b), in order to covalently attach the diazirine groups to the polymer strand;
(d) Purifying said polymer modified in c) on a Sephadex G-25 column or using other conventional purification and separation techniques in order to remove the unbound diazirine derivative molecules.

In a particular embodiment, the solvent used in the preparation of the polymer of the present invention is DMSO, and concentration of the diazirine compound is between 0.01 mM and 100 mM.

In yet another embodiment, method of tissue fixation comprises the steps of:
(a) Applying the composition of the present invention, being a hydrogel, film, patch or bondage, to a tissue to be fixed; and
(b) Irradiation of the applied tissue area with either UV or NIR light, which depends on the composition (whether it contains nanoparticles suitable for upconversion or not)

In still further embodiment, UV light wavelength is between 320 nm to 390 nm, the NIR light wavelength is between 800 nm to 1000 nm, and time of irradiation in both cases is less than 20 minutes.

Various embodiments of the invention may allow various benefits, and may be used in conjunction with various applications. The details of one or more embodiments are set forth in the accompanying figures and the description below. Other features, objects and advantages of the described techniques will be apparent from the description and drawings and from the claims.

BRIEF DESCRIPTION OF THE DRAWINGS

The present invention will be understood and appreciated more fully from the following detailed description taken in conjunction with the appended figures. Various exemplary embodiments are well illustrated in the accompanying figures with the intent that these examples not be restrictive. It will be appreciated that for simplicity and clarity of the illustration, elements shown in the figures referenced below are schematic. Of the accompanying figures.

DETAILED DESCRIPTION OF THE INVENTION

Figure 1:
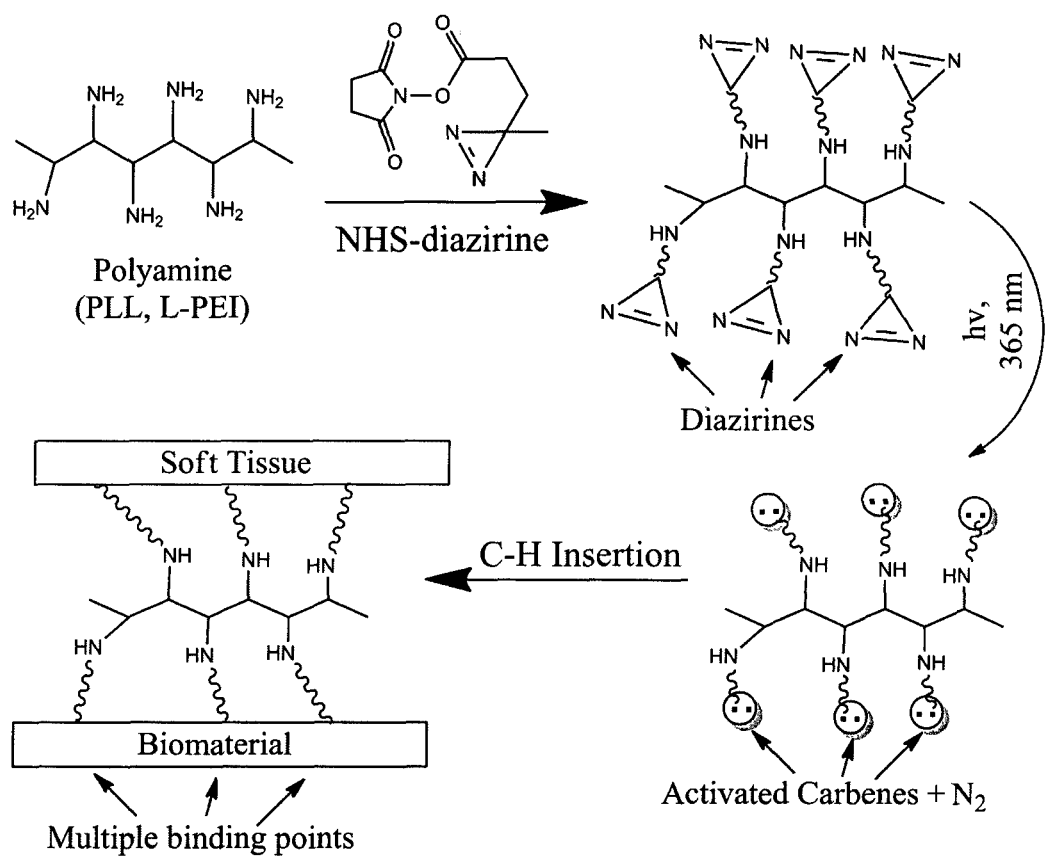
FIG. 1 is a synthetic route to poly-L-lysine crosslinked with diazirine groups used in the tissue fixation.

In the following description, various aspects of the invention will be described. For purposes of explanation, specific configurations and details are set forth in order to provide a thorough understanding of the invention. However, it will also be apparent to one skilled in the art that the invention may be practiced without the specific details presented herein. Furthermore, well-known features may be omitted or simplified in order not to obscure the invention.

It should be noted that although a portion of the discussion may relate to photoactive bioadhesive materials, compositions and methods, the present invention is not limited in this regard, and embodiments of the present invention may be used in conjunction with various other biomaterials, compositions and methods of treatment. As such, some embodiments of the invention may be used, for example, in conjunction with use of various biocompatible films, patches or bondages and in various surgery procedures. Some embodiments of the invention may be used not necessarily in the context of in vivo treatment.

"Biocompatible" material is defined as a natural or synthetic material having low variability, high purity, and no detectable biological reactivity as determined by biocompatibility tests. "Biocompatible polymer" is a natural or synthetic polymer having low variability, high purity, and no detectable biological reactivity as determined by biocompatibility tests. "Bioadhesive" or "bioadhesive material" means a synthetic material designed to adhere to biological tissues. By definition, bioadhesives are biocompatible materials.

A biocompatible polymer of the invention is built from a single strand of repeating units and up to 5,000 photoreactive groups covalently attached to said strand, and it has a molecular weight of up to 3 million Daltons. The crosslinked photoreactive groups are derivatives of diazirine.

The main polymeric strand or backbone can be any FDA-approved bioresorbable polymer selected from the group consisting of polyethylene glycol (PEG), PEG fatty acid esters, poly-L-lactic acid (PLLA), poly(lactide-co-glycolide) (PLGA), poly caprolactone (PCL), polyvinyl pyrrolidone (PVP), polyvinyl alcohol (PVA), collagen, chitosan, hydroxy propyl cellulose, polyamides, polyglycerol esters of fatty acids, polysaccharides, polyesters, and combinations thereof. The polysaccharide may be selected from the group consisting of dextran, chitosan, heparin, hyaluronic acid, alginates, starch, glycogen, amylose, amylopectin, cellulose, xylan, and numerous other natural and synthetic polysaccharides.

The specific example of an FDA-approved bioresorbable polymer is poly(lactic-co-glycolic acid) (PLGA) employed in a form of a thin film matrix. It has been incorporated into a number of drug delivery medical devices due to its numerous advantages, i.e. commercial availability in a range of formulations and controlled release for numerous therapeutics. The PLGA polymer can be blended for independent tailoring of both thin film mechanical properties to match soft tissue and controlled drug release.

The diazirine groups, which are crosslinked to the polymer, are compounds of the following formula.

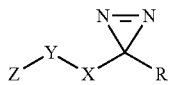

wherein

R is a hydrogen;

$C_1$-$C_8$ straight-chain or branched alkyl group, $C_2$-$C_8$ straight-chain or branched alkenyl or alkynyl group, or phenyl group substituted at any ring position with one or more the same or different $C_1$-$C_8$ straight-chain or branched alkyl group, phenyl or heterocyclic ring, which may be optionally substituted with one or more the same or different $C_1$-$C_8$ straight-chain or branched alkyl group, $C_1$-$C_8$ alkoxy group, $C_1$-$C_8$ alkoxycarbonyl group, carboxyl group, hydroxyl group, nitro group, halogen atom or amino group optionally mono or di-substituted with the same or different C1-C8 straight-chain or branched alkyl group;

methyl group substituted with 1-3 halogen atoms;

amino group optionally mono or di-substituted with the same or different $C_1$-$C_8$ straight-chain or branched alkyl group;

thiol or thioether group having the same or different $C_1$-$C_8$ straight-chain or branched alkyl group;

sulfone or sulfate group having the same or different $C_1$-$C_8$ straight-chain or branched alkyl group;

nitro, cyano, halogen, hydroxy, carboxylic acid or sulfonic acid group; or alkoxy or alkoxycarbonyl group having the same or different $C_1$-$C_8$ straight-chain or branched alkyl group;

X is a bond or 5-7 membered saturated cyclic or heterocyclic, aromatic or heteroaromatic ring unsubstituted or mono-, di- or tri-substituted with:

$C_1$-$C_8$ straight-chain or branched alkyl group, $C_2$-$C_8$ straight-chain or branched alkenyl or alkynyl group, or phenyl group substituted at any ring position with one or more the same or different $C_1$-$C_8$ straight-chain or branched alkyl group, phenyl or heterocyclic ring, which may be optionally substituted with one or more the same or different $C_1$-$C_8$ straight-chain or branched alkyl group, $C_1$-$C_8$ alkoxy group, $C_1$-$C_8$ alkoxycarbonyl group, carboxyl group, hydroxyl group, nitro group, halogen atom or amino group optionally mono or di-substituted with the same or different $C_1$-$C_8$ straight-chain or branched alkyl group;

methyl group substituted with 1-3 halogen atoms;

amino group optionally mono or di-substituted with the same or different $C_1$-$C_8$ straight-chain or branched alkyl group;

thiol or thioether group having the same or different $C_1$-$C_8$ straight-chain or branched alkyl group;

sulfone or sulfate group having the same or different $C_1$-$C_8$ straight-chain or branched alkyl group;

nitro, cyano, halogen, hydroxy, carboxylic acid or sulfonic acid group; or alkoxy or alkoxycarbonyl group having the same or different $C_1$-$C_8$ straight-chain or branched alkyl group;

Y is a bond or saturated and unsaturated $C_1$-$C_{500}$ straight-chain or branched alkyl, alkenyl or alkynyl group, wherein said chain may optionally incorporate at least one hetero atom, and may also comprise at least one substituent;

Z is any suitable functional group, such as halogen, amino, cyano, hydroxy, aldehyde, alkoxycarbonyl, N-amide, N-hydroxysuccinimide ester, maleimide or thiol.

The specific examples of the diazirine derivatives used in the present invention are:

3-phenyl-3-trifluoromethyl-3H-diazirine,
3-[3-(bromoacetylamino)phenyl]-3-trifluoromethyl-3H-diazirine,
3-[4-(bromoacetylamino)phenyl]-3-trifluoromethyl-3H-diazirine,
3-[2-methoxy,5-(bromoacetylamino)phenyl]-3-trifluoromethyl-3H-diazirine,
3-[2-cyano,5-(bromoacetylamino)phenyl]-3-trifluoromethyl-3H-diazirine,
3-[2-sulfo,5-(bromoacetylamino)phenyl]-3-trifluoromethyl-3H-diazirine,
3-[3-(bromomethyl)phenyl]-3-trifluoromethyl-3H-diazirine,
3-[4-(bromomethyl)phenyl]-3-trifluoromethyl-3H-diazirine,
3-[2-methoxy,5-(bromomethyl)phenyl]-3-trifluoromethyl-3H-diazirine,
3-[2-cyano,5-(bromomethyl)phenyl]-3-trifluoromethyl-3H-diazirine,
3-[2-sulfo,5-(bromomethyl)phenyl]-3-trifluoromethyl-3H-diazirine,
3-[3-aminophenyl]-3-trifluoromethyl-3H-diazirine,
3-[4-aminophenyl]-3-trifluoromethyl-3H-diazirine,
3-[2-methoxy,5-aminophenyl]-3-trifluoromethyl-3H-diazirine,
3-[2-cyano,5-aminophenyl]-3-trifluoromethyl-3H-diazirine, and
3-[2-sulfo,5-aminophenyl]-3-trifluoromethyl-3H-diazirine.

Reference is now made to FIG. 1 schematically showing synthetic route to the biocompatible polymer made of poly-L-lysine or linear polyethylenimine or polyamine crosslinked with diazirine groups followed by photoactivation and soft tissue fixation. Once activated with long-wave UV light, for instance at 365 nm, carbenes are formed, that instantly react and crosslink soft tissues and biomaterials by carbene-avidity through C—H insertion.

The novel biocompatible polymer used for bioadhesion was conceived after incorporating of key advances in the fields of plasma surface modification, diazirine-carbene chemistry, and antibody-based avidity binding concepts. This polymer allows one to trigger the tissue adhesion in situ, directly at the time and place the tissue fixation is required. The carbene insertion reaction employed is advantageous over other known covalent protein bonding methods, as it leaves the protein conformation relatively intact.

Current commercial bioadhesives employ adhesive mechanisms that are relatively inflexible and tend to have narrow applications. The biocompatible polymer of the present invention, based on photoactivation of diazirine residues, offers greater flexibility by allowing on demand activation of the diazirine-based surface binding. It is the only light-activated bioadhesive that is free of monomers and toxic photo-initiators. This polymer creates a fundamental shift in bioadhesive technology that would have considerable impact on medical implants—in vivo adhesion is a difficult hurdle that has yet to be overcome—especially in wet and protein-filled environments.

Treatment of surfaces by non-thermal plasmas is well known to create free radicals on biomaterial surfaces while leaving the bulk unaffected. The highly reactive nature of free radicals causes them to have a short half-life, on the order of milliseconds to seconds. However, even within this short life, free radicals react with nearly any polypeptide chains nearby, instantly creating new covalent bonds. As an example, the strong bioadhesion that results from argon plasma-treated thin films onto soft arterial tissue compared to the present methods of bioadhesion is discussed in the Experimental section below.

Free radicals are generally considered detrimental due to their implications in cellular aging. Recently however, several laboratories have revealed that proteins covalently immobilized by free radical mechanisms tend to retain protein conformation and have more functionality. This is a key observation in the design for soft, tissue bioadhesives—the higher the protein conformation retained, the lower the local tissue toxicity and inflammation is likely to be.

Although bioadhesives based on free radical covalent bonding are interesting, the plasma generation method is impractical due to the complexity of the plasma ovens and the short term half-lives of the radicals themselves (the majority are likely to be quenched upon atmospheric exposure). In order to take advantage of the free radical covalent bonding, a mechanism is needed to generate the radicals in situ (specifically at the time and place soft tissue bonding is desired). A unique functional group, diazirine, allows in situ formation of carbene, which can be seen as a type of free bi-radical.

Figure 2:
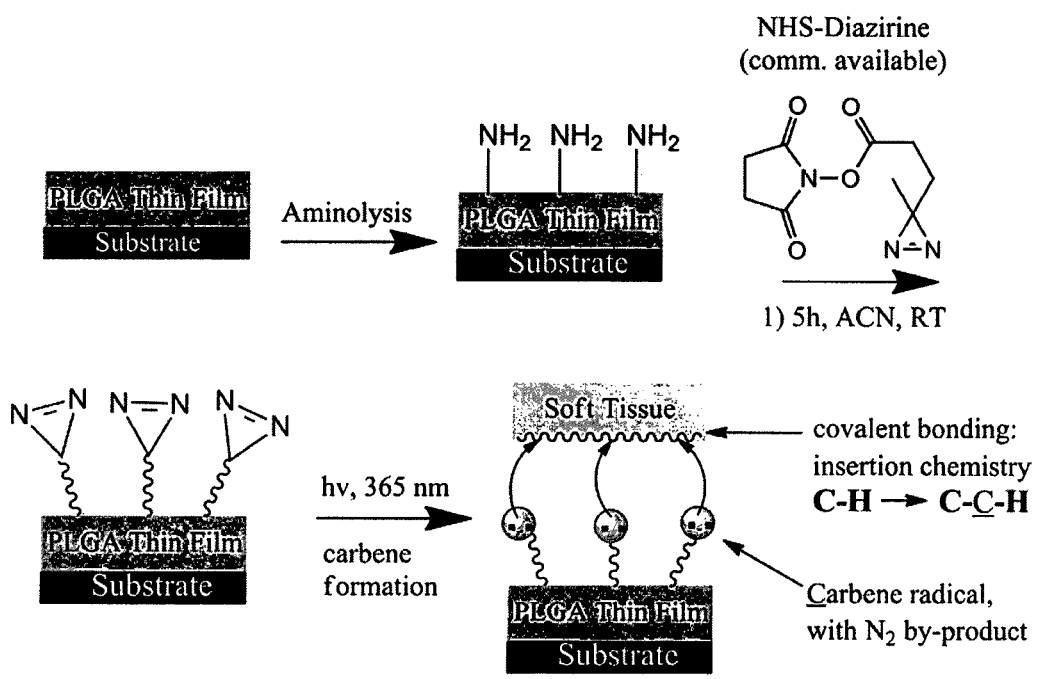
FIG. 2 is a schematic light activated tissue fixation through diazirine surface functionalization.

Reference is now made to FIG. 2, which shows on-demand, light activated surface adhesion through diazirine surface functionalization. The surface of PLGA thin films undergo aminolysis, leaving an amine-functionalized surface that readily reacts with NHS-diazirine compound. Upon UV light excitation at 365 nm, the diazirine compound decomposes to an extremely reactive carbene and evolves nitrogen gas. The carbene instantly reacts via insertion reaction with any nearby polypeptide chains of soft tissues—a fact that has made it widely popular as a photoaffinity reagent for protein labelling studies.

The diazirine photoactive functional groups allow in situ free radical carbene generation with no toxic byproducts for relatively harmless protein backbone covalent bonding. Many photoactive compounds exist, such as azides, diazo compounds, benzophenone, anthraquinone, diaryl diazomethanes, and psoralene. However, it has been found that among all these molecules, diazirines have the highest photolinking efficiencies with the fastest reaction times—a very strong endorsement for their development as bioadhesives. This fast and efficient crosslinking is due to the diazirine functional group. It is rapidly converted to carbene and harmless nitrogen gas upon exposure to long wavelength UV light. The high reactivity of carbene, which is similar to that of free radicals, allows immediate covalent bonding via insertion reaction, whereby the carbene basically inserts itself into an already existing C—H bond. This type of C—H insertion is relatively harmless within protein backbones—a fact that makes diazirines (along with their small size) particularly popular for photoaffinity labelling to study ligand-receptor, ligand-enzyme, and protein-protein interactions.

The diazirine mechanism of adhesion has many advantages over other adhesion mechanisms. For example, cyanoacrylate cannot be activated on demand, often begins to polymerize at the slightest amount of moisture, and tends to be toxic after degradation. Light activated acrylate or epoxide polymerization based bioadhesives tend to have high front temperatures (causing thermal damage) and leave behind toxic monomers by-products, as well as photoinitiators. The diazirine functional group leaves no monomer or photoinitiator by-products after curing.

With the use of commercially available NHS-diazirines, novel poly-diazirines can be easily synthesized by employing antibody inspired avidity-type binding mechanisms in a one-pot synthesis. No syntheses of poly-diazirines have yet to be reported in the scientific literature, despite the ease of synthesis and the promising potential of the present technology.

"Avidity" is a term to define the combined strength of multiple bonding interactions simultaneously with one or more targets. Poly-diazirine bioadhesion attempts to avidity bond soft-tissue to soft tissue or soft tissue to other relevant biomaterials. The poly-diazirine based bioadhesive could be tailored via numerous methods, depending on the application. For example, interfacial bioadhesion strength could be adjusted by varying the density of the diazirine functional groups on the polymer backbone or by controlling the intensity/time of the light activation, so only the needed fraction of diazirines are activated into carbenes.

Environmental instability and light sensitivity of the diazirine-based bioadhesives can be controlled through barrier packaging for limited contact of atmosphere and light, until the diazirine bioadhesive is needed, moments before tissue adhesion. Alkyl diazirines are known to have more intramolecular side products leading to no adhesion by minimizing intermolecular crosslinking reactions with the desired protein backbones. This can be addressed by optimizing the surface concentration, rate of diazirine group to carbene (via UV intensity), or simply switching to awl trifluorodiazirines. The latter are known to be much more stable than their corresponding alkyl analogues, and more reliable in photoaffinity labelling, but are not commercially available because of their more demanding synthesis. Therefore, their use as bioadhesives has never been suggested before.

Diazirines, particularly, aryl trifluorodiazirines have another essential advantage over other photoaffinity groups, such as diaryl diazomethanes, of being excited at the longer UV wavelength. It should be noted that excitation at 300 nm and below must be avoided in order to prevent tissue damage.

In light of the above, the biocompatible polymer of the invention has the following advantages over commercially available bioadhesives, such as cyanoacrylates and fibrin-based bioadhesives:

Can stick to wet or dry materials;
Activated on demand with immediate photocuring;
Adapted to existing biomaterials that have been previously FDA approved;

Adhesion mechanism leaves protein in tissues relatively intact;

Avoids any toxic photoinitiators;

Degradation has no toxic by-products; and

Multiple functional groups can be easily converted in the reactive diazirine groups, including primary and secondary amines, ketones, and aldehydes.

The bioadhesive composition may further comprise the polymer of the present invention and suitable solvents, surfactants, stabilizers, fillers and other additives. The additives may be anti-inflammatory drugs, anti-proteases, antibiotics, and/or anti-restenosis compounds. The composition can be in a form of hydrogel, biocompatible film, patch or bondage.

Bioadhesive hydrogels could have multiple uses in surgeries, particularly in anastomosis procedures, where two tubes or lumens must be joined. For example, gastrointestinal surgeries towards cancer removal, obesity treatments, and bowel obstructions. Blood vessel anastomosis is in significant need of new bioadhesives. Sutures currently limit blood vessel anastomosis to vessels of more than 1 mm in diameter, which limits reattachment of amputated limbs.

The bioadhesive hydrogels can be prepared from many common biocompatible polymers and polyglycans, for example dextran, chitosan, heparin, hyaluronic acid, alginates, starch, glycogen, amylose, amylopectin, cellulose, xylan, and numerous other natural and synthetic polysaccharides. Polysaccharides can be functionalized with diazirines through primary and secondary amines groups, carbonyl groups such as aldehyde groups, ketones, and carboxylic acids. Most preferably are the primary amines and aldehyde groups. Most polysaccharides can be turned into poly-aldehydes through oxidation reactions such as treatment with sodium periodate, treatment with nitrous acid, etc.

Bioadhesive thin films have numerous applications across the medical spectrum. Biodegradable thin films of the present invention offer a more cost effective replacement for sutures, band aids, or dressings. Drug impregnated diazirine-based bioadhesives offer local drug delivery to a variety of soft-tissues, thereby eliminating systemic drug side effects and first-pass liver metabolism, while allowing delivery of acid-labile therapeutics (which cannot be taken orally). The novel approach inherent in the diazirine-based bioadhesive design allows adhesion even in wet, protein filled environments—a claim no other bioadhesive has yet to make. This allows targeting of the vasculature ailments by piggybacking the bioadhesive thin films of the invention on modified angioplasty balloon catheters.

In addition, the composition may contain metallic particles of size less than 50 micron made of rare earth elements, such as lanthanide group elements, including but not limited to scandium, yttrium, lanthanum, cerium, praseodymium, neodymium, promethium, samarium, europium, gadolinium, terbium, dysprosium, holmium, erbium, thulium, ytterbium, and lutetium. These metallic particles are able to convert NIR to UV light, among other wavelengths. While the UV light is limited to a few mm of penetration depth at most, NIR light is able to transverse more than 1 cm of bone tissue and more than 5 cm of soft tissue. Accordingly, the composition of the invention is UV or NIR transparent, having transparency less than 1 optical density unit per 1 centimeter.

The metal particles can be coated with anionic or cationic coating comprising fatty acids, silica, polyethylene glycol, pluronics, poloxamers, polydopamine, polylysine or any suitable peptide.

Figure 3:
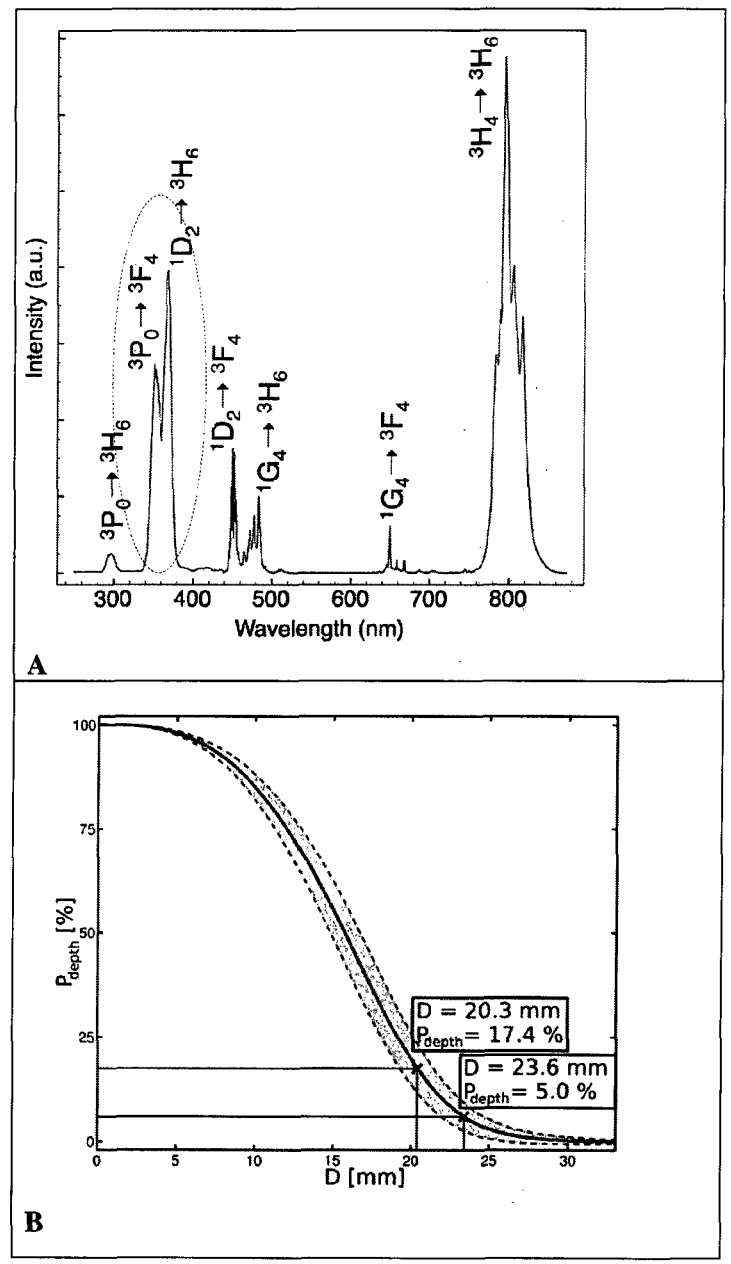
FIG. 3A is a prior-art upconversion luminescence spectrum of lanthanide oleate-capped LiYF4:Tm3+ nanoparticles in toluene after irradiation at 980 nm (F. Vetrone et al., Chemistry of Materials 2009; 21:1847-51). The circled region shows the wavelengths needed for diazirine photo-activation.
FIG. 3B is a prior-art penetration depth of NIR light through the cranium bone and tissues (F. B. Haeussinger et al., PLoS One 2011; 6:e26377).

Reference is now made to prior-art FIGS. 3A and 3B, which explain the powerful concept of the upconversion. FIG. 3A displays a prior-art upconversion luminescence spectrum of lanthanide oleate-capped LiYF4:Tm3+ nanoparticles in toluene after irradiation at 980 nm. The circled region shows the wavelengths needed for diazirine photoactivation.

Upconversion luminescence is a physical process where light of lower frequencies, for instance near-infrared (NIR), is converted to light of higher frequencies, for example UV light. As shown on FIG. 3A, the lanthanide metallic particles are able to convert 980 nm light to other spectrums, with a major intensity band in the UV region, where diazirine derivatives can be photoactivated.

With the use of NIR light, deeper tissue penetration of light radiation is achieved. NIR light absorption coefficients and scattering coefficients tend to be higher than the UV and visible light spectrum, therefore they can shine through bone thickness of 1 cm or more and tissue thickness of 5 cm or more. FIG. 3B shows a prior-art penetration depth of NIR light through the cranium bone and tissues. As it can be seen, at about 20 mm of depth, 17% light intensity is still present.

Thus, by combining metallic particles into the bioadhesive thin films or hydrogels of the invention, these bioadhesive compositions can be photoactivated through NIR lasers, which are commercially available in laser LED pen devices. This opens applications that have been limited by previous adhesive formulations, for example bone, ligament, and tendon adhesives for carpals, metacarpals, finger and foot phalanges, tarsus, metatarsals, and limb bones.

The lanthanide nanoparticles also exhibit no apparent cytotoxic effects. This would allow the bioadhesive compositions of the invention to be activated after syringe or laparoscopic insertion, widening the applicability towards novel therapeutic implants. A typical operation involves syringe injection of the bioadhesive implant into a bone fracture, followed by on-demand adhesion activation with irradiation of NIR laser LED. This outpatient procedure would greatly increase speed and reduce cost of orthopedic surgeries. The use of bone fixtures, such as wires, pins, and buttress plates, and their associated complications would be greatly reduced. For example, in orthopaedic applications, syringe-injectable bone casts for fractures can be made, with no limb immobilizing plaster casts required.

In still additional embodiment, the composition may further comprise aligned nanofibers of biodegradable polymer, such as collagen or gelatin, for matching biomechanics of soft tissues. The soft tissues, such as of vein and arteries, are known to exhibit a non-linear anisotropy—the elastic modulus increases exponentially with strain in the radial-orientation, but not in the axial-orientation.

Figure 4:
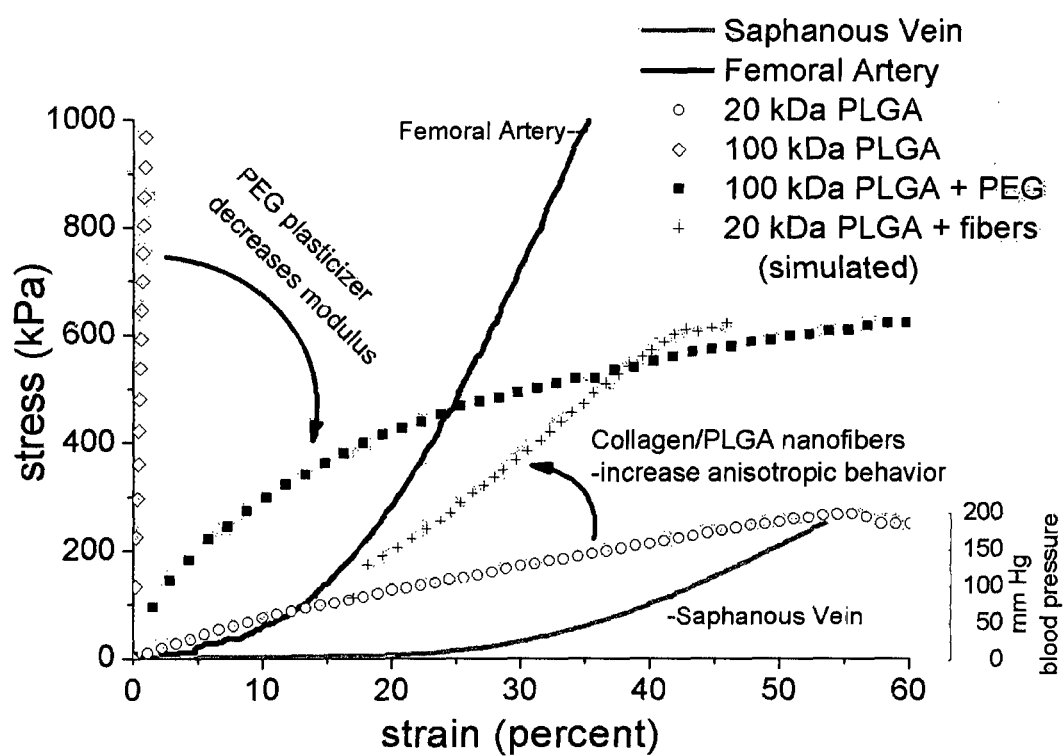
FIG. 4 is a comparison between soft tissue biomechanics of the prior art radial-orientated saphenous vein (re-plotted from R. Hashizume et al., Biomaterials 2010; 31:3253-65) and femoral artery (re-plotted from P. J. Prendergast et al., J. Biomech. Eng. 2003; 125:692-9) and the PLGA thin films of the present invention.

Reference is now made to FIG. 4 showing a comparison between soft tissue biomechanics of the prior art radial-orientated saphenous, vein and femoral artery and the PLGA thin films of the present invention. As noted above, adhesion failure often arises from elastic modulus mismatch—the two materials have different stress vs. strain properties that cause shear failure on the bioadhesive or substrate. By matching the bioadhesive modulus to that of the soft tissue, strong and lasting adhesion is possible. FIG. 4 displays two soft tissue biomechanics as examples of low modulus tissues, the saphenous vein and femoral artery. Human arteries vary nonlinearly from 400 to 1500 kPa depending on the stress applied. Bioadhesive thin films according to the present invention demonstrate elastic modulus within this range, by applying either additives to high modulus, high molar mass PLGA thin films, or by employing low molar mass PLGA.

Both examples are demonstrated in FIG. 4 with 100 kDa PLGA, 100 kDa PLGA+10% PEG, and 20 kDa PLGA. Each has an elastic modulus of 13000 kPA, 750 kPa, and 580 kPa, respectively. The latter two exemplify the control that is achieved towards matching the elastic modulus of soft tissue and are within the elastic modulus in the range of 250-1100 kPa that the prior-art techniques have chosen for vascular grafts.

Bioadhesives towards organ sealants or vascular tissues is the preferable application, due to the plethora of sealants needed, ease of reach with common catheters, or both (sealants for air/lung or dura mater/fluid leakages, trauma haemostasis, or intestinal anastomoses).

Thus, incorporation of the aligned nanofibers of biodegradable polymers within the matrix of the bioresorbable polymer, such as PLGA, can mimic this anisotropy of the tissue under treatment. Collagen nanofibers are preferable, since the raw material is commercially available and has been well characterized. The collagen nanofibers are easily incorporated into PLGA matrices since they are insoluble in organic solvents, and embedded within the PLGA thin films, much like rebar in concrete. Besides the additive mechanical properties of the PLGA/collagen composite, embedded nanofibers can reduce cracking and flaking of the PLGA matrices as they are resorbed, degraded, or both while adhered to the soft tissue. This composite method gives an excellent opportunity for further refinement of the mechanical properties should it be necessary. For example, gelatin fibers (gelatin is derived from collagen), is already known to increase modulus and tensile strength in resorbable polyesters. Should tailoring the aligned collagen fibers by thickness alone become unfeasible, the orientation of the embedded nanofibers can provide an alternative approach of tuning the mechanical properties.

The adhesives properties of the bioadhesive compositions of the invention before and after tissue placement are characterized through biaxial tensile testing capabilities down to sample sizes of 3 mm sq, using the biaxial biomaterial instrument, for example Biotester 5000 from Cellscale Inc.

According to the embodiments of the invention, the composition may be used in surgery, such as gastrointestinal surgery towards cancer removal, anastomoses procedures, such as blood vessel anastomoses wherein two tubes or lumens must be joined, tissue fixation, suture sealing and replacement, treatment of lung punctures, body lumen punctures or leaks, cerebrospinal fluid membrane damages, obesity treatments, and bowel obstructions.

A method for the preparation of the biocompatible polymer of the present invention involves the following steps:
(a) Preparing a solution of said biocompatible polymer having concentration of 0.1 to 100 mg/ml at pH 7.2;
(b) Dissolving said diazirine compound in a suitable organic within the concentration range of 0.01 to 100 mM;
(c) Mixing and reacting the solution of said biocompatible polymer prepared in a) with the solution of the diazirine derivative prepared in b), in order to covalently attach the diazirine groups to the polymer strand;
(d) Purifying said polymer modified in c) on a Sephadex G-25 column or using other conventional purification and separation techniques in order to remove the unbound diazirine derivative molecules.

The preferable solvent used in the above preparation is DMSO, and concentration of the diazirine compound is between 0.01 mM and 100 mM.

According to another embodiment of the invention, method of tissue fixation comprises the following steps:
(a) Applying the composition of the present invention, being a hydrogel, film, patch or bondage, to a tissue to be fixed; and
(b) Irradiation of the applied tissue area with either UV or NIR light, which depends on the composition (whether it contains nanoparticles suitable for upconversion or not)

The wavelength range of the UV irradiation is between 320-390 nm, the NIR light wavelength is between 800 nm to 1000 nm, and time of irradiation in both cases is less than 20 minutes.

Experimental Example

Figure 5:
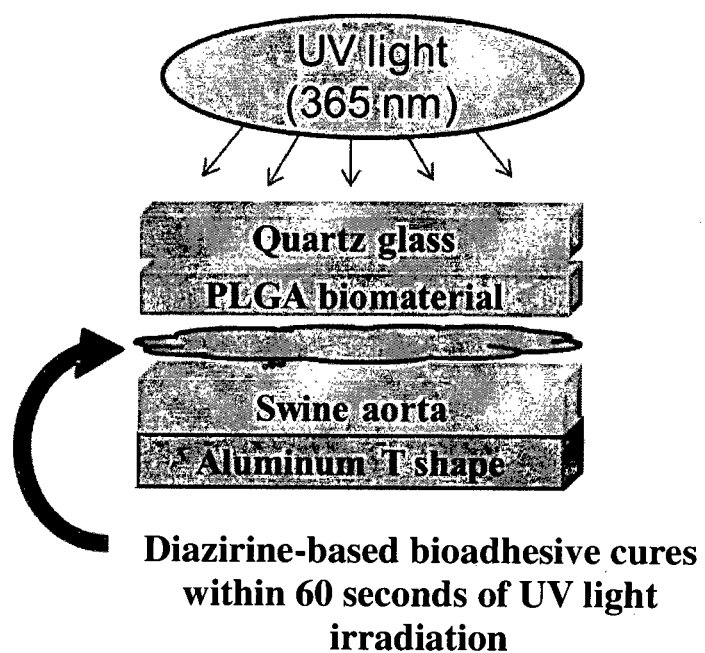
FIG. 5 is a schematic representation of an application method of PLGA thin films covered with PLGA-diazirine polymer compressed into swine aorta tissues and irradiated with UV light.
Figure 6:
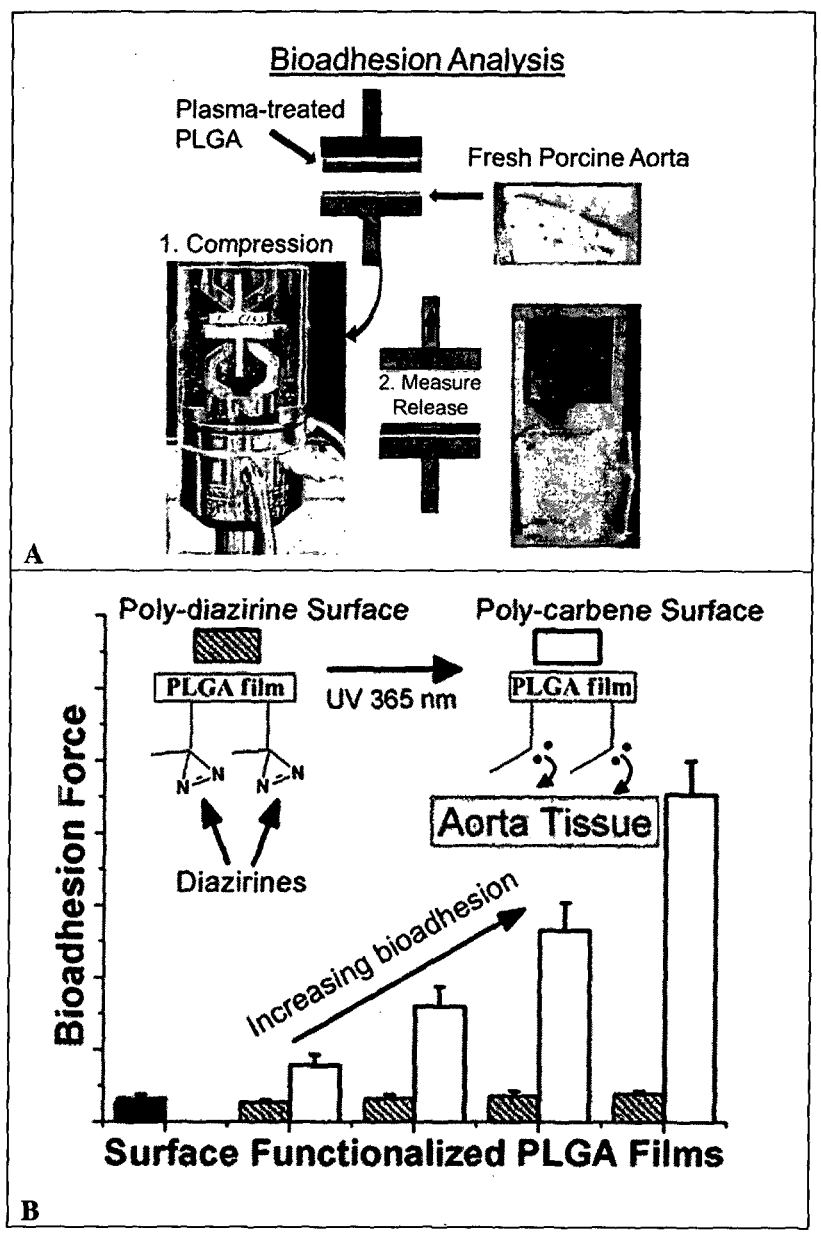
FIG. 6A is a bioadhesion analysis of surface functionalized PLGA thin films compressed into swine aorta in vitro at forces representative of angioplasty balloon catheters, through argon plasma or UV-activated surface grafted PLGA-diazirine adhesive biomaterial.
FIG. 6B is a comparison between the bioadhesion forces of the prior art surface grafted PLGA-diazirine adhesive biomaterial with increasing surface concentrations of diazirine with and without UV-activation on swine aorta soft tissues.

Comparison of Plasma-Initiated and PLL-Diazirine Surface Functionalization on the PLGA Resorbable Thin Films The present experiment shows the comparison between free radical and PLGA-diazirine based adhesion mechanisms. The latter has yielded a potential breakthrough for resorbable thin films towards soft tissue bioadhesion. Reference is now made to FIGS. 5, 6A and 6B.

FIG. 5 schematically demonstrates an application method of PLGA thin films of the invention covered with polyamine-diazirine polymer compressed into swine aorta tissues and irradiated with UV light. FIG. 6A displays a representative bioadhesion analysis of the surface functionalized PLGA thin films compressed into swine aorta in vitro at forces representative of angioplasty balloon catheters, through surface grafted PLGA-diazirine adhesive biomaterial. FIG. 6B is a comparison between the bioadhesion forces of the prior art surface grafted PLGA-diazirine adhesive biomaterial with increasing surface concentrations of diazirine with and without UV-activation on swine aorta soft tissues.

The results clearly display much stronger adhesion directly on vascular tissues, even in aqueous environments, for the thin films of the invention coated with poly-L-lysine-diazirine in comparison to the argon plasma-related surface functionalization. The bioadhesive forces shown in FIG. 6B are comparable in strength to topical skin adhesives.

These investigations were performed on the smooth PLGA thin film surface topologies, and it is expected that advanced surface topologies can raise the bioadhesion several times over.

Although portions of the discussion herein may relate to bioadhesion, the present invention is not limited in this regard, and may include, for example, additional surgical procedures.

A biocompatible polymer, composition and methods in accordance with some embodiments of the invention may be used, for example, in conjunction with a device which may be inserted into a human body. However, the scope of the present invention is not limited in this regard. For example, some embodiments of the invention may be used in conjunction with a device which may be inserted into a non-human body or an animal body.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A biocompatible polymer comprising a single strand of repeating units and up to 5,000 photoreactive groups covalently attached to said strand, wherein said polymer is comprised in a poly(lactide-co-glycolide) (PLGA) film, wherein the PLGA film is covered with said polymer, wherein said polymer has a molecular weight of up to 3 million Daltons, and wherein said photoreactive groups are derivatives of diazirine, wherein the polymer is a polyamide.

2. The polymer according to claim 1, wherein said diazirine derivative is a compound of the following formula:

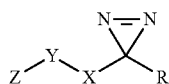

wherein
R is
- a hydrogen;
- $C_1$-$C_8$ straight-chain or branched alkyl group, $C_2$-$C_8$ straight-chain or branched alkenyl or alkynyl group, or phenyl group substituted at any ring position with one or more the same or different $C_1$-$C_8$ straight-chain or branched alkyl group, phenyl or heterocyclic ring, which may be optionally substituted with one or more the same or different $C_1$-$C_8$ straight-chain or branched alkyl group, $C_1$-$C_8$ alkoxy group, $C_1$-$C_8$ alkoxycarbonyl group, carboxyl group, hydroxyl group, nitro group, halogen atom or amino group optionally mono or di-substituted with the same or different $C_1$-$C_8$ straight-chain or branched alkyl group;
- methyl group substituted with 1-3 halogen atoms;
- amino group optionally mono or di-substituted with the same or different $C_1$-$C_8$ straight-chain or branched alkyl group;
- thiol or thioether group having the same or different $C_1$-$C_8$ straight-chain or branched alkyl group;
- sulfone or sulfate group having the same or different $C_1$-$C_8$ straight-chain or branched alkyl group;
- nitro, cyano, halogen, hydroxy, carboxylic acid or sulfonic acid group; or
- alkoxy or alkoxycarbonyl group having the same or different $C_1$-$C_8$ straight-chain or branched alkyl group;

X is a bond or 5-7 membered saturated cyclic or heterocyclic, aromatic or heteroaromatic ring unsubstituted or mono-, di- or tri-substituted with:
- $C_1$-$C_8$ straight-chain or branched alkyl group, $C_2$-$C_8$ straight-chain or branched alkenyl or alkynyl group, or phenyl group substituted at any ring position with one or more the same or different $C_1$-$C_8$ straight-chain or branched alkyl group, phenyl or heterocyclic ring, which may be optionally substituted with one or more the same or different $C_1$-$C_8$ straight-chain or branched alkyl group, $C_1$-$C_8$ alkoxy group, $C_1$-$C_8$ alkoxycarbonyl group, carboxyl group, hydroxyl group, nitro group, halogen atom or amino group optionally mono or di-substituted with the same or different $C_1$-$C_8$ straight-chain or branched alkyl group;
- methyl group substituted with 1-3 halogen atoms;
- amino group optionally mono or di-substituted with the same or different $C_1$-$C_8$ straight-chain or branched alkyl group;
- thiol or thioether group having the same or different $C_1$-$C_8$ straight-chain or branched alkyl group;
- sulfone or sulfate group having the same or different $C_1$-$C_8$ straight-chain or branched alkyl group;
- nitro, cyano, halogen, hydroxy, carboxylic acid or sulfonic acid group; or
- alkoxy or alkoxycarbonyl group having the same or different $C_1$-$C_8$ straight-chain or branched alkyl group;

Y is a bond or saturated and unsaturated $C_1$-$C_{500}$ straight-chain or branched alkyl, alkenyl or alkynyl group, wherein said chain may optionally incorporate at least one hetero atom, and may also comprise at least one substituent;

Z is any suitable functional group, such as halogen, amino, cyano, hydroxy, aldehyde, alkoxycarbonyl, N-amide, N-hydroxysuccinimide ester, maleimide or thiol.

3. The polymer according to claim 2, wherein said diazirine derivative is selected from the group consisting of:
- 3-phenyl-3-trifluoromethyl-3H-diazirine,
- 3-[3-(bromoacetylamino)phenyl]-3-trifluoromethyl-3H-diazirine,
- 3-[4-(bromoacetylamino)phenyl]-3-trifluoromethyl-3H-diazirine,
- 3-[2-methoxy, 5-(bromoacetylamino)phenyl]-3-trifluoromethyl-3H-diazirine,
- 3-[2-cyano, 5-(bromoacetylamino)phenyl]-3-trifluoromethyl-3H-diazirine,
- 3-[2-sulfo, 5-(bromoacetylamino)phenyl]-3-trifluoromethyl-3H-diazirine,
- 3-[3-(bromomethyl)phenyl]-3-trifluoromethyl-3H-diazirine,
- 3-[4-(bromomethyl)phenyl]-3-trifluoromethyl-3H-diazirine,
- 3-[2-methoxy, 5-(bromomethyl)phenyl]-3-trifluoromethyl-3H-diazirine,
- 3-[2-cyano, 5-(bromomethyl)phenyl]-3-trifluoromethyl-3H-diazirine,
- 3-[2-sulfo, 5-(bromomethyl)phenyl]-3-trifluoromethyl-3H-diazirine,
- 3-[3-aminophenyl]-3-trifluoromethyl-3H-diazirine,
- 3-[4-aminophenyl]-3-trifluoromethyl-3H-diazirine,
- 3-[2-methoxy, 5-aminophenyl]-3-trifluoromethyl-3H-diazirine,
- 3-[2-cyano, 5-aminophenyl]-3-trifluoromethyl-3H-diazirine,
- 3-[2-sulfo, 5-aminophenyl]-3-trifluoromethyl-3H-diazirine,
- 3-stilbenyl-3-trifluoromethyl-3H-diazirine,
- 3-[4-(N,N'-dimethylamino)stilbenyl]-3-trifluoromethyl-3H-diazirine,
- 3-[4-methoxystilbenyl]-3-trifluoromethyl-3H-diazirine,
- 3-[4-hydroxystilbenyl]-3-trifluoromethyl-3H-diazirine,
- 3-[4-aminostilbenyl]-3-trifluoromethyl-3H-diazirine,
- 3-[4-chlorostilbenyl]-3-trifluoromethyl-3H-diazirine,
- 3-[4-bromostilbenyl]-3-trifluoromethyl-3H-diazirine,
- 3-[4-nitrostilbenyl]-3-trifluoromethyl-3H-diazirine,
- 3-[4-cyanostilbenyl]-3-trifluoromethyl-3H-diazirine,
- 3-[4-carbomethoxystilbenyl]-3-trifluoromethyl-3H-diazirine,
- 3-[4-carboxystilbenyl]-3-trifluoromethyl-3H-diazirine,
- 3-[3,5-dimethoxystilbenyl]-3-trifluoromethyl-3H-diazirine,
- 3-[3,5-dinitrostilbenyl]-3-trifluoromethyl-3H-diazirine,
- 3-[3,5-dihydroxystilbenyl]-3-trifluoromethyl-3H-diazirine, 3-naphthyl-3-trifluoromethyl-3H-diazirine,
3-pyridinyl-3-trifluoromethyl-3H-diazirine,
3-anthryl-3-trifluoromethyl-3H-diazirine, and
3-pyrenyl-3-trifluoromethyl-3H-diazirine.

4. A bioadhesive composition comprising the polymer of claim 1 and suitable solvents, surfactants, stabilizers, fillers and other additives.

5. The composition according to claim 4, wherein said additives are anti-inflammatory drugs, anti-proteases, antibiotics, and/or anti-restenosis compounds.

6. The composition according to claim 4, wherein said composition is in a form of hydrogel, biocompatible film, patch or bondage.

7. The composition according to claim 4 further comprising aligned nanofibers of biodegradable polymer.

8. The composition according to claim 7, wherein said polymer is collagen or gelatin.

9. The composition according to claim 4, wherein said composition is UV transparent.

10. The composition according to claim 9 having transparency less than 1 optical density unit per 1 centimeter.

11. The composition according to claim 4 further comprising any alginate-based polymer, such as alginate-pyrrole or alginate-biotin, thus providing additional properties to the biomaterial, such as increased affinity and conductivity.

12. A method for tissue fixation comprising the steps of:
(a) Applying the composition of claim 4 to a tissue to be fixed; and
(b) Irradiation of the applied tissue area with UV light.

13. The method according to claim 12, wherein the UV light wavelength is between 320 nm to 390 nm, and time of irradiation is less than 20 minutes.

14. The composition according to claim 4 comprising metallic particles of size less than 50 micron.

15. The composition according to claim 14, wherein said particles comprises rare earth elements, such as lanthanide group elements, including but not limited to scandium, yttrium, lanthanum, cerium, praseodymium, neodymium, promethium, samarium, europium, gadolinium, terbium, dysprosium, holmium, erbium, thulium, ytterbium, and lutetium.

16. The composition according to claim 14, wherein said metal particles are coated with anionic or cationic coating.

17. The composition according to claim 16, wherein said coating comprises fatty acids, silica, polyethylene glycol, pluronics, poloxamers, polydopamine, polylysine or any suitable peptide.

18. The composition according to claim 14 further comprising aligned nanofibers of biodegradable polymer.

19. The composition according to claim 18, wherein said polymer is collagen or gelatin.

20. The composition according to claim 14, wherein said composition is NIR transparent.

21. The composition according to claim 20 having transparency less than 1 optical density unit per 1 centimeter.

22. A method for tissue fixation comprising the steps of:
(a) Applying the composition of claim 14 to a tissue to be fixed; and
(b) Irradiation of the applied tissue area with NIR light.

23. The method according to claim 22, wherein the NIR light wavelength is between 800 nm to 1000 nm, and time of irradiation is less than 20 minutes.

24. A method for the preparation of the polymer of claim 1, comprising the steps of:
(a) Preparing a solution of said biocompatible polymer having concentration of 0.1 to 100 mg/ml at pH 7.2;
(b) Dissolving said diazirine compound in a suitable organic within the concentration range of 0.01 to 100 mM;
(c) Mixing and reacting the solution of said biocompatible polymer prepared in a) with the solution of the diazirine derivative prepared in b), in order to covalently attach the diazirine groups to the polymer strand;
(d) Purifying said polymer modified in c) on a Sephadex G-25 column or using other conventional purification and separation techniques in order to remove the unbound diazirine derivative molecules.

25. The method according to claim 24, wherein the solvent is DMSO.

26. The method according to claim 24, wherein concentration of the diazirine compound is between 0.01 mM and 100 mM.

27. The polymer according to claim 1, wherein the polyamide is poly-L-lysine.

28. A method of using a bioadhesive composition comprising the polymer of claim 1 and suitable solvents, surfactants, stabilizers, fillers and other additives in surgery, such as gastrointestinal surgery towards cancer removal, anastomoses procedures (including end-to-end anastomoses), such as blood vessel anastomoses wherein two tubes or lumens must be joined, tissue fixation, suture sealing and replacement, treatment of lung punctures, body lumen punctures or leaks, cerebrospinal fluid membrane damages, obesity treatments, and bowel obstructions, fixing flat electrodes to heart tissue during open heart, and surgery patches containing drugs such as in gastrointestinal system.

29. A method of treating post-surgery gastrointestinal anastomoses, such as end-to-end anastomoses, blood vessel anastomoses wherein two tubes or lumens must be joined, fixed tissues, sealing and replacing sutures, lung punctures, body lumen punctures or leaks, cerebrospinal fluid membrane damages, obesity and bowel obstructions, the method comprising administering a bioadhesive composition comprising the polymer of claim 1 and suitable solvents, surfactants, stabilizers, fillers and other additives to the subject.

30. A method of using a bioadhesive composition comprising the polymer of claim 1 and suitable solvents, surfactants, stabilizers, fillers and other additives for the preparation of a formulation for fixing flat electrodes to heart tissue during open heart surgery, and for surgery patches containing drugs.

* * * * *